(12) United States Patent
Suwa et al.

(10) Patent No.: US 10,722,195 B2
(45) Date of Patent: Jul. 28, 2020

(54) RADIOGRAPHIC APPARATUS INCLUDING HEAT-GENERATING MEMBER, LOWER HOUSING INCLUDING RECESS, AND HEAT-TRANSFER PORTION DISPOSED BETWEEN HEAT-GENERATING MEMBER AND RECESS

(71) Applicant: CANON KABUSHIKI KAISHA, Tokyo (JP)

(72) Inventors: Hidetomo Suwa, Machida (JP); Akiya Nakayama, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 107 days.

(21) Appl. No.: 16/020,861

(22) Filed: Jun. 27, 2018

(65) Prior Publication Data

US 2019/0011574 A1  Jan. 10, 2019

(30) Foreign Application Priority Data

Jul. 7, 2017  (JP) .................. 2017-133794

(51) Int. Cl.
*A61B 6/00* (2006.01)
*G01T 1/20* (2006.01)
*G01T 1/24* (2006.01)
*G01T 1/16* (2006.01)
(Continued)

(52) U.S. Cl.
CPC .......... *A61B 6/4283* (2013.01); *A61B 6/4405* (2013.01); *A61B 6/4488* (2013.01); *G01T 1/16* (2013.01); *G01T 1/2018* (2013.01); *G03B 42/04* (2013.01); *A61B 6/42* (2013.01); *A61B 6/4208* (2013.01); *A61B 6/4233* (2013.01); *A61B 6/4241* (2013.01); *A61B 6/44* (2013.01); *A61B 6/4411* (2013.01); *A61B 6/4452* (2013.01); *G03B 17/55* (2013.01)

(58) Field of Classification Search
CPC ....... A61B 6/42; A61B 6/4208; A61B 6/4233; A61B 6/4241; A61B 6/4283; A61B 6/44; A61B 6/4405; A61B 6/4411; A61B 6/4452; A61B 6/4488; G01T 1/2018
USPC ..................... 378/98.8, 189; 250/370.09
See application file for complete search history.

(56) References Cited

U.S. PATENT DOCUMENTS 7,429,737 B2 * 9/2008 Wojcik ................. A61B 6/4233
                                                      250/370.09
7,449,696 B2 * 11/2008 Joshi .................... G01T 1/2018
                                                      250/363.03
(Continued)

FOREIGN PATENT DOCUMENTS

| JP | 2006-215028 A | 8/2006 |
| JP | 2011-043390 A | 3/2011 |
| JP | 2012-042302 A | 3/2012 |

*Primary Examiner* — Allen C. Ho
(74) *Attorney, Agent, or Firm* — Canon U.S.A., Inc. IP Division (57) ABSTRACT

A radiographic apparatus includes a radiation detector, a heat generating member, a lower housing including a recess disposed at a position facing the heat generating member, and a heat transfer portion for transferring heat from the heat generating member to the lower housing. The heat transfer portion is disposed between the heat generating member and the recess, and is continuously disposed along the inner surface of the lower housing in a region other than the recess.

7 Claims, 6 Drawing Sheets

(51) Int. Cl.
*G03B 42/04* (2006.01)
*G03B 17/55* (2006.01)

(56) References Cited

U.S. PATENT DOCUMENTS

| | | | | |
|---|---|---|---|---|
| 7,495,226 B2* | 2/2009 | Jadrich | | G01T 1/20 250/370.09 |
| 7,687,790 B2* | 3/2010 | Utschig | | A61B 6/102 250/505.1 |
| 7,800,065 B2* | 9/2010 | Konkle | | G01T 1/2018 250/336.1 |
| 8,172,461 B2* | 5/2012 | Liu | | A61B 6/4283 378/114 |
| 8,213,573 B2* | 7/2012 | Liu | | A61B 6/4283 378/62 |
| 8,319,506 B2* | 11/2012 | Liu | | A61B 6/4283 324/691 |
| 8,366,319 B2* | 2/2013 | Kawasaki | | G01T 1/2018 378/189 |
| 8,581,202 B2* | 11/2013 | Yamada | | G01T 1/2018 250/370.09 |
| 8,592,774 B2* | 11/2013 | Suwa | | A61B 6/4405 250/370.09 |
| 8,653,826 B2* | 2/2014 | Liu | | G01R 31/69 324/538 |
| 8,690,426 B2* | 4/2014 | Liu | | G03B 42/02 250/370.09 |
| 8,710,448 B2* | 4/2014 | Luhta | | G01T 1/2018 250/370.11 |
| 8,748,836 B2* | 6/2014 | Sato | | A61B 6/4283 250/370.09 |
| 8,766,200 B2* | 7/2014 | Konkle | | A61B 6/102 250/370.08 |
| 8,779,907 B2* | 7/2014 | Liu | | A61B 6/4405 340/384.1 |
| 8,853,644 B2* | 10/2014 | Nakahashi | | A61B 6/00 250/394 |
| 8,901,505 B2* | 12/2014 | Kobayashi | | G01T 1/2018 250/369 |
| 8,967,861 B2* | 3/2015 | Mizuno | | A61B 6/4233 378/169 |
| 9,006,671 B2* | 4/2015 | Noguchi | | A61B 6/4405 250/370.04 |
| 9,011,000 B2* | 4/2015 | Tagawa | | A61B 6/10 250/370.09 |
| 9,119,584 B2* | 9/2015 | Sato | | H04N 5/32 |
| 9,161,730 B2* | 10/2015 | Ham | | A61B 6/4283 |
| 9,322,934 B2* | 4/2016 | Ogura | | G01T 1/2006 |
| 9,380,988 B2* | 7/2016 | Kitano | | A61B 6/4283 |
| 9,700,271 B2* | 7/2017 | Horiuchi | | A61B 6/4405 |
| 9,820,703 B2* | 11/2017 | Wojcik | | A61B 6/4233 |
| 9,883,839 B2* | 2/2018 | Nariyuki | | A61B 6/0414 |
| 9,978,234 B2* | 5/2018 | Kano | | A61B 6/4283 |
| 10,119,859 B2* | 11/2018 | Suzuki | | A61B 6/102 |
| 10,274,613 B2* | 4/2019 | Suzuki | | G03B 42/02 |
| 10,317,540 B2* | 6/2019 | Akamatsu | | G01T 1/2006 |
| 10,451,503 B2* | 10/2019 | Kikuchi | | G01T 1/00 |
| 10,488,534 B2* | 11/2019 | Kawaguchi | | G01T 1/244 |
| 10,520,804 B2* | 12/2019 | Miyoshi | | G03B 42/025 |
| 2017/0090044 A1 | 3/2017 | Suzuki | | |

\* cited by examiner

RADIOGRAPHIC APPARATUS INCLUDING HEAT-GENERATING MEMBER, LOWER HOUSING INCLUDING RECESS, AND HEAT-TRANSFER PORTION DISPOSED BETWEEN HEAT-GENERATING MEMBER AND RECESS

BACKGROUND

Field

The present disclosure relates to a radiographic apparatus applied to a medical-image diagnosis apparatus, a non-destructive inspection apparatus, an analyzer, and the like.

Description of the Related Art

A radiographic apparatus incorporating a radiation detector including a semiconductor sensor mounted thereon is known. In this apparatus, the intensity distribution of the radiation transmitted through an object can be converted into an electric signal by the radiation detector, and the obtained electric signal can be processed and displayed on a monitor as an image.

In moving image radiographing with a radiographic apparatus, since the temperature inside the apparatus rises compared to still image radiographing, a mechanism for lowering the temperature inside the apparatus is provided. Japanese Patent Laid-Open No. 2012-042302 discloses a cassette for radiographing that guides heat generated by a heat generating member through a thermally conductive material to a housing having an opening for heat radiation. Japanese Patent Laid-Open No. 2006-215028 discloses a photoelectric conversion device in which a flexible cable on which an integrated circuit (IC) is mounted is fixed to a housing and heat generated from the IC is thereby released to the housing.

Recently, due to the improvement in the sensitivity of radiation detectors, the occurrence of image artifacts due to the temperature distribution. (unevenness) in the apparatus and the temperature change besides mere temperature rise is a problem. The conventional heat radiation mechanism is not always sufficient as a countermeasure against this problem, and is not sufficient as a safety measure when the operator or the subject touches the apparatus.

The present disclosure ensures safety without giving discomfort to an operator or a subject by improving heat radiation efficiency.

SUMMARY

In an aspect of the present disclosure, a radiographic apparatus includes a radiation detector, a heat generating member, a lower housing including a recess disposed at a position facing the heat generating member, and a heat transfer portion for transferring heat from the heat generating member to the lower housing. The heat transfer portion is disposed between the heat generating member and the recess, and is continuously disposed along an inner surface of the lower housing in a region other than the recess.

Further features will become apparent from the following description of exemplary embodiments with reference to the attached drawings.

DESCRIPTION OF THE EMBODIMENTS

Hereinafter, embodiments will be described with reference to the drawings. In the embodiments, X-rays are used as radiation, but alpha rays, beta rays, gamma rays, particle beams, cosmic rays and the like can also be used.

Embodiment 1

Figure 1:
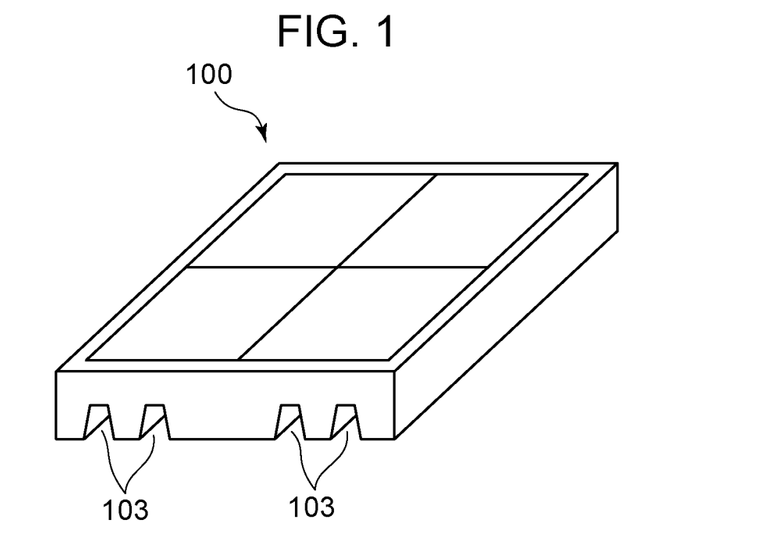
FIG. 1 is a perspective view of a radiographic apparatus according to Embodiment 1.
Figure 2:
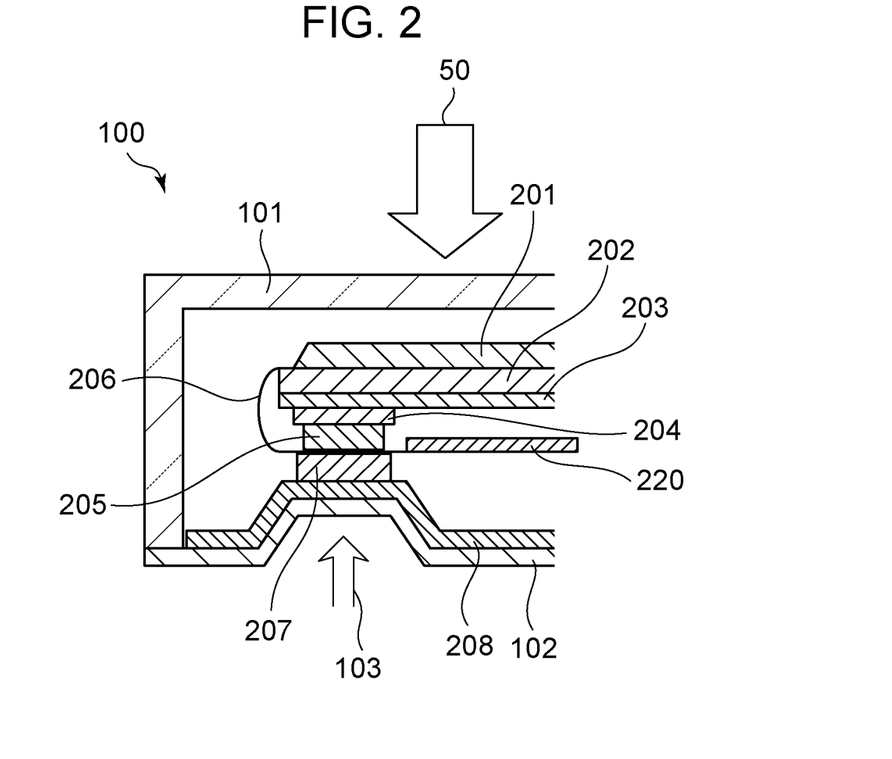
FIG. 2 is a partial cross-sectional view of the radiographic apparatus according to Embodiment 1.

FIG. 1 illustrates an external view of a radiographic apparatus 100, and FIG. 2 illustrates a part of a cross-section of the radiographic apparatus 100. In FIG. 2, an upper housing 101, a phosphor 201, a radiation detector 202, and a base 203 are stacked when viewed from the radiation incidence direction 50. On the back side of the radiation detector 202, a lower housing 102 is disposed. The radiation incident region (front part) of the upper housing 101 is required to have high radiation transmittance and strength, and is frequently made of a carbon fiber material. The part other than the incident region is often made of an aluminum-based or magnesium-based alloy, but is also made of a carbon fiber material.

Radiation emitted from a radiation generating apparatus (not illustrated) passes through a subject and is incident on the radiographic apparatus 100. The incident radiation is converted into light by the phosphor 201, and converted into an electric signal by the radiation detector 202 composed of a semiconductor sensor. Besides the indirect type radiation detection method in which radiation is converted into light and then converted into an electric signal, the direct type radiation detection method in which radiation is directly converted into an electric signal can also be used. Between the upper housing 101 and the phosphor 201, a foam material or foam body is disposed as a cushioning material (not illustrated) against external impacts.

The housing is composed of the upper housing 101 and the lower housing 102, and the radiation detector 202 and the base 203 are disposed inside the housing. The upper housing 101 and the lower housing 102 can be integrated without joint structure. The base 203 is disposed on the back surface of the radiation detector 202. The base 203 is fixed to the radiation detector 202 with an adhesive tape, adhesive, or the like, and supports the radiation detector 202. The base 203 can be made of a material having a high thermal conductivity and a high radiation absorption rate, and is made of an alloy or a carbon fiber material.

An electric board 220 for driving the radiation detector 202 and processing an electric signal output from the radiation detector 202 to output an image signal is disposed on the back surface of the base 203. A flexible printed circuit 206 for transmitting and receiving drive signals and electric signals is disposed between the radiation detector 202 and the electric board 220.

An IC 205 is mounted on the flexible printed circuit 206. When the radiation detector 202 is driven, the IC 205 performs high-speed signal processing, and therefore generates heat. A heat insulating member 204 is disposed between the IC 205 and the base 203 so that the heat generated in the IC 205, which is a heat generating member, does not move to the radiation detector 202 side.

Heat transfer portions 207 and 208 are disposed between the IC 205 and the lower housing 102. The heat transfer portions 207 and 208 can be made of a graphite sheet or silicon in order to have a high thermal conductivity and to prevent a short circuit due to contact with the IC 205. As long as the heat transfer portions 207 and 208 are not in contact with the IC 205, the heat transfer portions 207 and 208 can be made of a metal, such as copper or aluminum. The heat transfer portion 207 also includes a function of holding the radiation detector 202 in the lower housing 102. In this example, the heat transfer portions 207 and 208 are illustrated as separate members, but can be formed as an integral member.

A recess 103 is formed at a position facing the IC 205 in the back surface portion of the lower housing 102. The heat transfer port ion 208 is disposed between the IC 205 and the recess 103, and is also continuously disposed in the region other than the recess 103 along the inner surface of the lower housing 102. Heat generated in the IC 205 is transferred to the heat transfer portion 208 through the heat transfer portion 207 and released to the recess 103, and diffuses quickly around the recess 103 to be released. By disposing the recess 103, the distance between the IC 205, which is a heat generating portion, and the lower housing 102 is shortened, and the heat radiation capability is increased.

The heat transfer portion 208 is disposed on the entire inner surface of the lower housing 102 as illustrated by die shaded portion in FIG. 5A described below. Alternatively, as illustrated by the shaded portion in FIG. 5B, the heat transfer portion 208 is disposed in the inner surface region excluding the short side end portions of the lower housing 102. The heat transfer portion 208 can be disposed in the inner surface region excluding both short and long side end portions of the lower housing 102.

The recess 103 functions as a holding portion when the operator carries the radiographic apparatus 100 or when the subject holds the radiographic apparatus 100 during radiographing. At that time, heat generated in the IC 205 is not only released to the recess 103, but also diffused to a wider area around the recess 103. Therefore, when an operator's or subject's fingers are placed in the recess 103, the heat sensed by the fingers is reduced, and operability is not impaired.

In the back surface portion of the lower housing 2, the amount of heat transferred to the region inside the recess 103 can be greater than the amount of heat transferred to the region outside the recess 103. If a heat insulating member (not illustrated) is disposed on the surface of the heat transfer portion 208 on the side opposite to the lower housing 102 except for the region fixed to the heat transfer portion 207, the temperature rise in the housing can be suppressed.

Embodiment 2

Figure 3A:
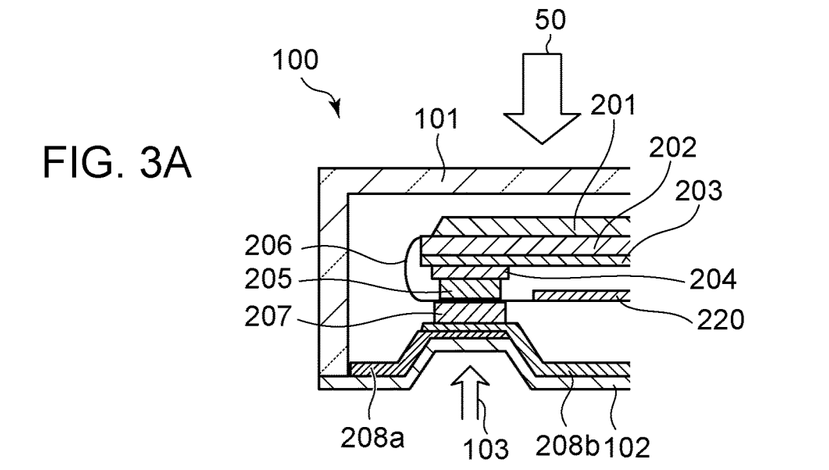
FIGS. 3A to 3C are partial cross-sectional views of a radiographic apparatus according to Embodiment 2.

FIG. 3A is a cross-sectional view of a radiographic apparatus 100 according to this embodiment. The heat transfer portion 208 is composed of heat transfer portions 208a and 208b with different thermal conductivities. The thermal conductivity of the heat transfer portion 208b is higher than that of the heat transfer portion 208a. That is, the thermal conductivity of the portion extending from the recess is higher than that of the portion between the IC 205 and the recess 103. Accordingly, the heat generated in the IC 205 is released to the housing through the heat transfer portions 207, 208a, and 208b, but the amount of heat at this time is greater in the heat transfer portion 208b than in the heat transfer portion 208a. This enables releasing the heat generated in the IC 205 toward the center of the lower housing 102. The center is the center of a plane normal to the incident direction 50 in the radiographic apparatus 100.

Figure 3B:
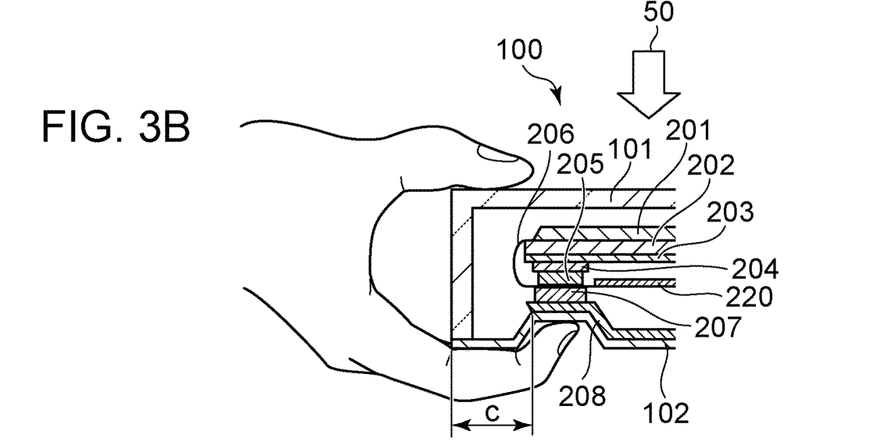
Figure 3C:
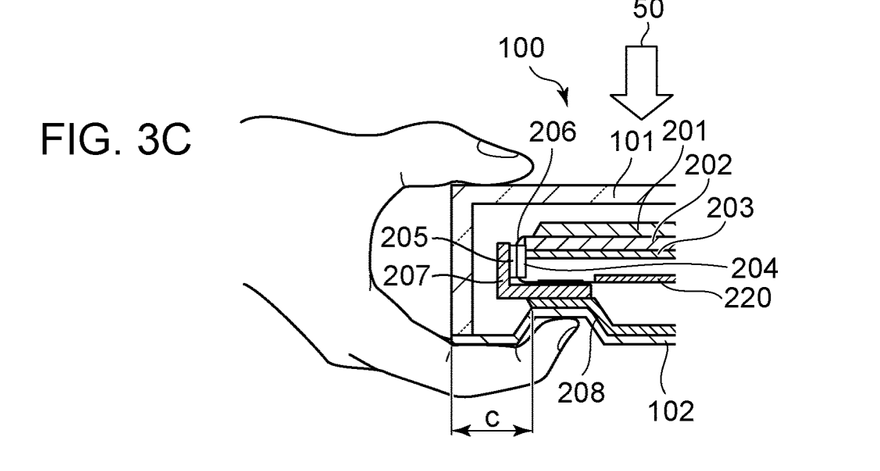

In this example, two heat transfer portions with different thermal conductivities are disposed, but three or more heat transfer portions can be provided. As illustrated in FIG. 3B, the heat generated in the IC 205 may not be released to the region c which is the peripheral portion of the lower housing 102. As illustrated in FIG. 3C, the heat transfer portion 207 can be held by the lower housing 102 at the bottom portion and the side portion of the radiation detector 202.

Embodiment 3

Figure 4A:
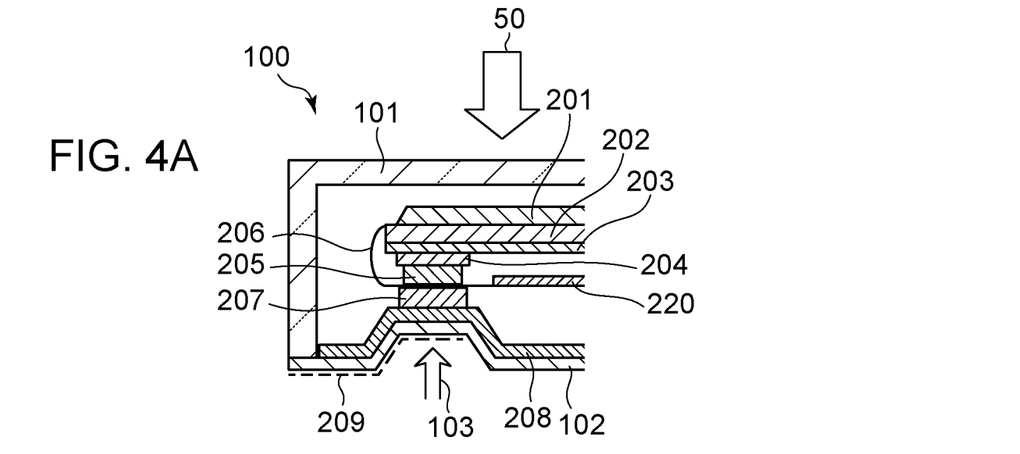
FIGS. 4A to 4O are partial cross-sectional views of a radiographic apparatus according to Embodiment 3.
Figure 4B:
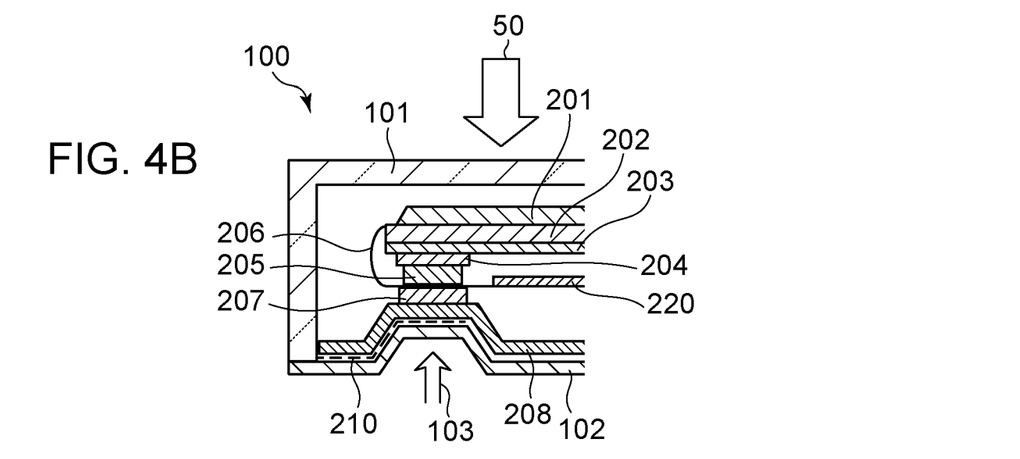

FIG. 4A is a cross-sectional view of a radiographic apparatus 100 according to this embodiment. A heat insulating member 209 is disposed on the outer surface side of the lower housing 102. As a result, even if the temperature of the lower housing 102 rises due to heat generation of the IC 205, the operator and the subject can be protected from heat, and safety can be ensured. In FIG. 4B, a heat insulating member 210 is disposed on the inner surface side of the lower housing 102. The heat insulating member 209 is disposed at the recess 103 and at a position from the recess 103 to the end portion of the lower housing 102.

Figure 4C:
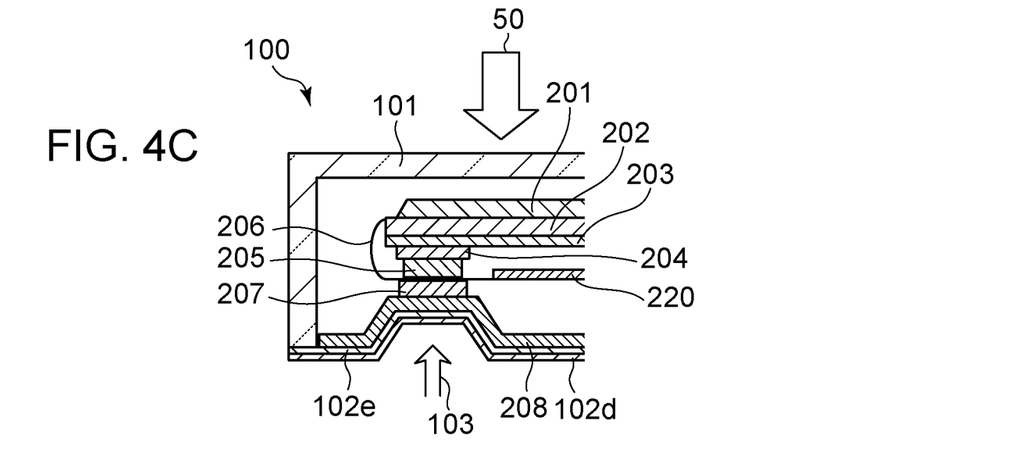

As illustrated in FIG. 4C, the lower housing 102 can be composed of two materials 102d and 102e with different thermal conductivities. In this example, the thermal conductivity is changed in the thickness direction of the lower housing 102, but the thermal conductivity can be changed in the direction of a plane normal to the radiation incident direction.

Embodiment 4

This embodiment relates to the shape of the recess 103 of the radiographic apparatus 100 illustrated in Embodiments 1 to 3 and a radiographic system employing the radiation imaging apparatus 100.

Figure 5A:
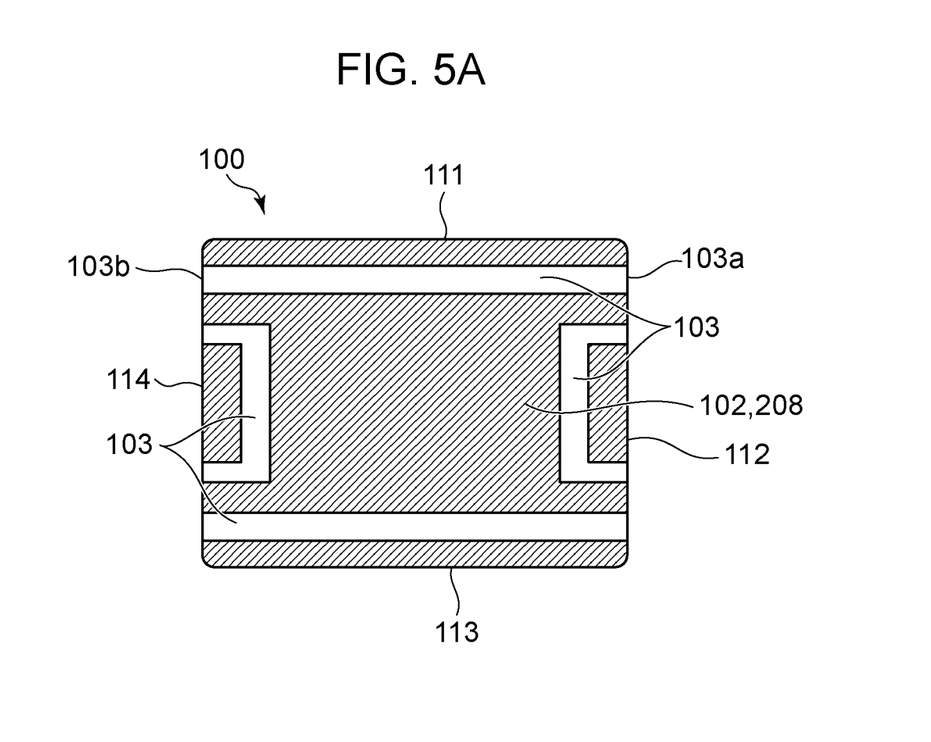
FIGS. 5A and 5B are views of a radiographic apparatus according to Embodiment 4.
Figure 5B:
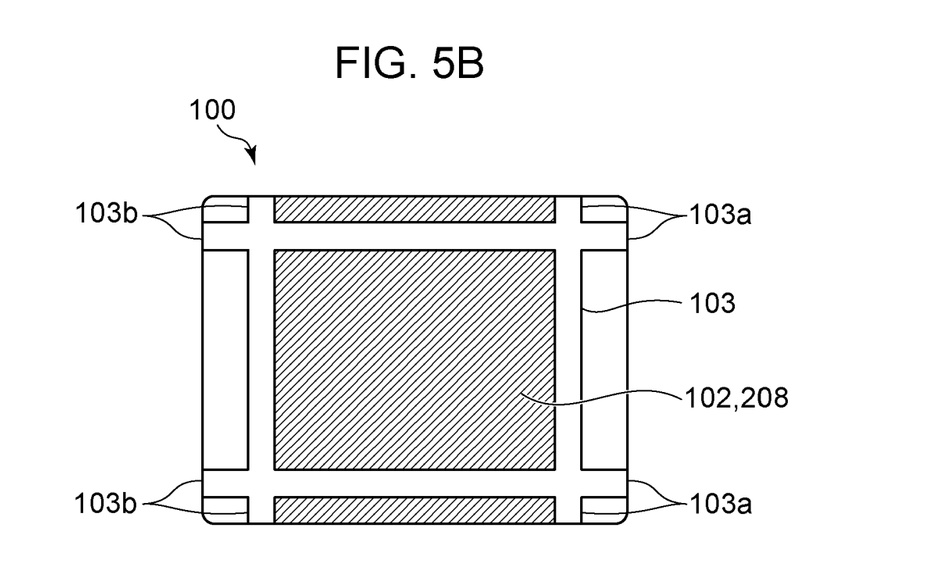

FIGS. 5A and 5B are views of a radiographic apparatus 100 according to this embodiment, and illustrate a surface opposite to the incident surface of the lower housing 102. As illustrated in FIG. 5A, the end portions 103a and 103b of the recess 103 reach the side surfaces 112 and 114 of the radiographic apparatus 100. In FIG. 5B, the end portions 103a and 103b of the recess 103 reach the four side surfaces 111, 112, 113, and 114 of the radiographic apparatus 100.

Figure 6:
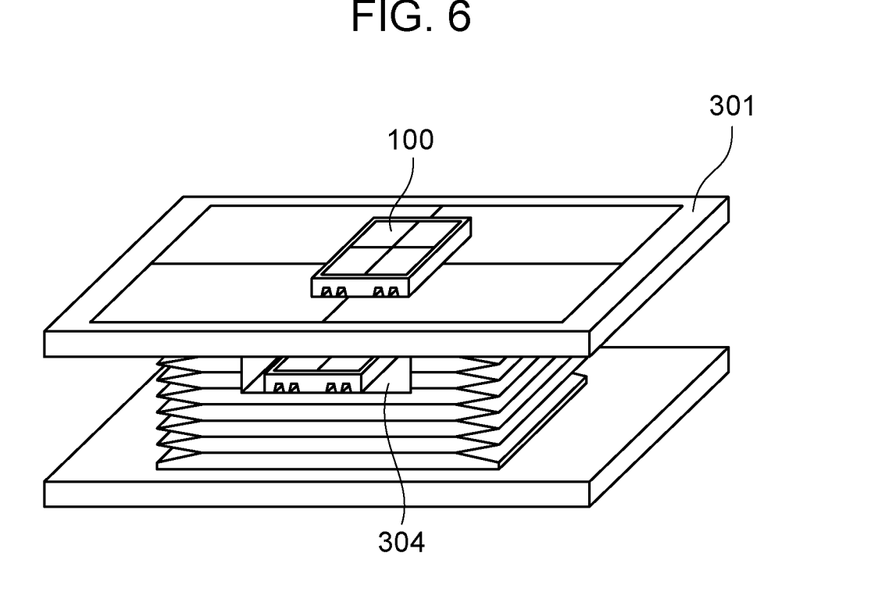
FIG. 6 is a schematic diagram of a radiographic system according to Embodiment 4.

FIG. 6 illustrate a case where the radiographic apparatus 100 is used by placing it on a bed table 301, and a case where the radiographic apparatus 100 is used when it is housed in a container 304 under the bed table 301.

Figure 7A:
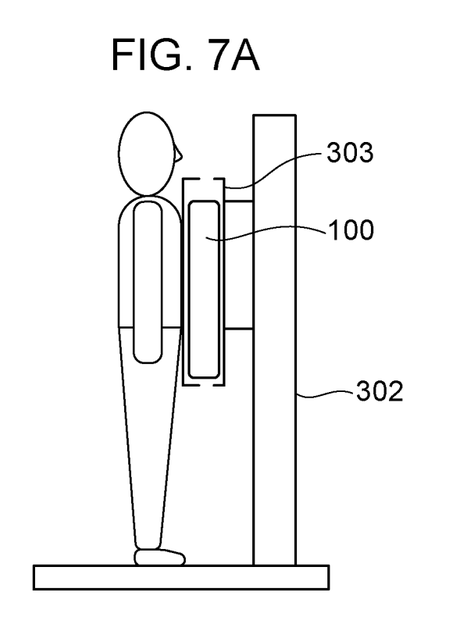
FIGS. 7A to 7C are schematic diagrams of another radiographic system according to Embodiment 4.
Figure 7B:
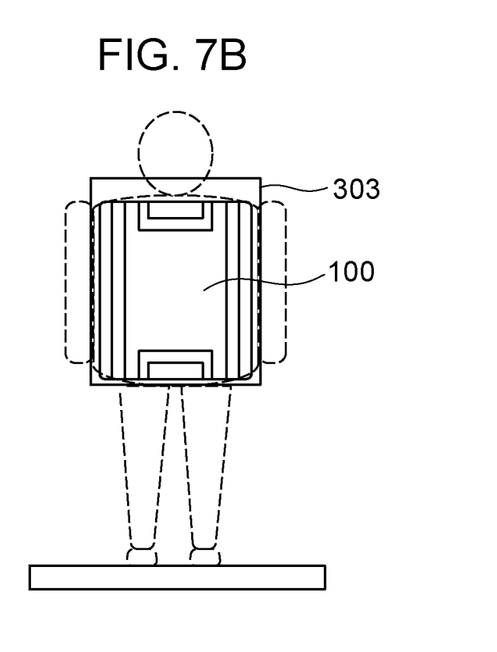
Figure 7C:
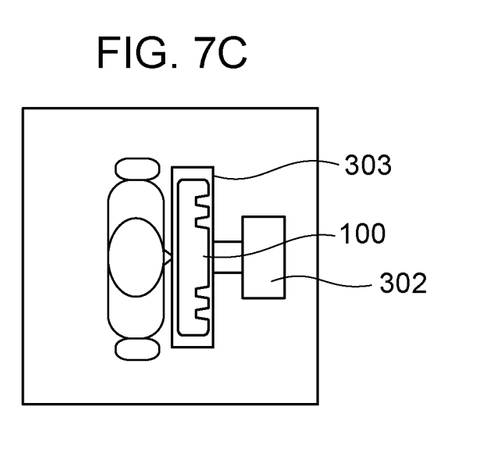

FIGS. 7A to 7C illustrate a case where the radiographic apparatus 100 is used by loading it inside a standing position stand 302. The standing position stand 302 includes a fixed container 303 in which the radiographic apparatus 100 is housed. At this time, another member, such as the wall of the container, is closely disposed on the back surface of the radiographic apparatus 100, and the heat radiation efficiency can decrease. Power consumption increases and heat generation increases, especially during moving image taking. Even in such a case, since the recess 103 reaches the side surface of the upper housing 101, heat is released to the air localized in the recess 103, and the temperature rise of the radiographic apparatus 100 can be suppressed. The warmed air moves out of the recess 103 due to an ascending air current or the like, fresh air enters the recess 103, and the heat radiation efficiency is thereby improved. A unit that forcibly replaces air can be provided.

Therefore, the radiographic apparatus 100 of the present disclosure is suitably used in a system for radiographing in a supine position or a standing position.

While exemplary embodiments have been described, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2017-133794 filed Jul. 7, 2017, which is hereby incorporated by reference herein in its entirety.

What is claimed is:

1. A radiographic apparatus comprising:
    a radiation detector;
    a heat generating member;
    a lower housing including a recess disposed at a position facing the heat generating member; and
    a heat transfer portion for transferring heat from the heat generating member to the lower housing,
    wherein the heat transfer portion is disposed between the heat generating member and the recess, and is continuously disposed along an inner surface of the lower housing in a region other than the recess.

2. The radiographic apparatus according to claim 1, wherein the lower housing is located on a back side of the radiation detector as viewed from a direction of incidence of radiation, and wherein the heat transfer portion is disposed on an entire inner surface of the lower housing.

3. The radiographic apparatus according to claim 1 further comprising a housing, wherein the radiation detector is disposed inside the housing comprising the lower housing and an upper housing, and the recess is disposed to reach a side surface of the upper housing.

4. The radiographic apparatus according to claim 3, wherein the upper housing and the lower housing are integrated.

5. The radiographic apparatus according to claim 1, wherein a thermal conductivity of a part of the heat transfer portion extending from the recess is greater than a thermal conductivity of a part of the heat transfer portion between the heat generating member and the recess.

6. The radiographic apparatus according to claim 1, wherein the heat transfer portion is disposed to extend from the recess toward a center of the lower housing.

7. The radiographic apparatus according to claim 1 further comprising a heat insulating member disposed on one or more of an outer surface side and the inner surface side of the lower housing, at the recess, and at a position from the recess to an end portion of the lower housing.

* * * * *